United States Patent [19]

Alfaro

[11] Patent Number: 5,310,544
[45] Date of Patent: May 10, 1994

[54] METHOD FOR TREATING TEETH TO REMOVE FLUOROSIS STAINS

[76] Inventor: Jose F. Alfaro, Independencia 2000, Privada Alfaro Fracc. San Pedro, Irapauto, Gto., Mexico, Z.P. 36520

[21] Appl. No.: 938,751

[22] Filed: Sep. 1, 1992

Related U.S. Application Data

[63] Continuation-in-part of Ser. No. 690,048, Apr. 23, 1991, abandoned.

[51] Int. Cl.⁵ .......................... A61K 7/16; A61K 9/68; A61C 15/00
[52] U.S. Cl. ........................................ 424/49; 424/48; 433/216
[58] Field of Search ...................... 424/48, 49; 433/216

[56] References Cited

U.S. PATENT DOCUMENTS 4,400,372  8/1983  Muhler.
4,780,083  10/1988  Croll ................................. 438/216

FOREIGN PATENT DOCUMENTS 1591982  9/1990  U.S.S.R..

OTHER PUBLICATIONS

Goldstein, R. E., Esthetics in Dentistry, J. B. Lippincott Co., Phila., 1976, pp. 37-38.

McCloskey, R. J., JADA, vol. 109, A Technique for Removal of Fluorisis Stains, Jul. 1984, pp. 63-64.

Kendell, R. L., Hydrochloric Acid Removal of Brown Fluorosis Stains, Quintessence Jnl., vol. 20, #11, 1989, pp. 837-839.

Jagger, R. G., Hydrochloric Acid-Pumice Treatment, Restorative Dentistry, Feb. 1990, pp. 4-6.

Wong, M., A Clinical Comparison of Treatments for Endemic Dental Fluorosis, J. of Endo, 17(17), Jul. 1991, pp. 343-345.

Belkhir, M. S., A New Concept for Removal of Dental Fluorosis Stains, Jnl. of Endodontics, vol. 17, No. 6, Jun. 1991, pp. 288-292.

*Primary Examiner*—Michael G. Wityshyn
*Assistant Examiner*—Ralph Gitomer
*Attorney, Agent, or Firm*—Pravel, Hewitt, Kimball & Krieger

[57] ABSTRACT

The invention provides a method for the removal or reduction of tooth enamel stains due to fluorosis. The method includes a step of treating a surface of an isolated stained tooth with an abrasive-free solution of hydrochloric acid, having a concentration of from about 6-12N, for a period of time sufficient to significantly reduce staining of the tooth, without removal enamel from the treated surface. Thereafter, any residual acid on the tooth surface is neutralized.

3 Claims, No Drawings

METHOD FOR TREATING TEETH TO REMOVE FLUOROSIS STAINS

RELATED APPLICATIONS

This Application is a continuation in part of U.S. Ser. No. 07/690,048 filed Apr. 23, 1991, abandoned.

BACKGROUND OF THE INVENTION

1. Field Of The Invention

This invention relates to a method for the cleansing of tooth enamel which is stained by fluorosis. More particularly, this invention relates to the application of acid solutions to the stained tooth enamel thereby removing or reducing the stain.

2. Description Of The Art

One of the serious dental cosmetic problems arises due to fluorosis. Fluorosis, or mottled enamel, is a form of enamel hypoplasia resulting from ingested fluorides during the tooth formation period. The severity of the enamel defects appears to be related to the amount of fluoride ingested so that, for example, when the fluoride level is lower than one part per million, there is little chemically significant mottling, and as fluoride levels go up, so too does the severity of mottling. There is a wide variation in the clinical appearance of teeth affected by fluorosis or mottling. The affected teeth are those that, during their formative periods, were subjected to abnormally high levels of fluoride. The enamel defects are invariably bilateral, involving similar teeth in all four quadrants. While there is no pain associated with fluorosis, the defects have been heretofore largely permanent and when severe may be disfiguring.

Although not all cases of fluorosis are disfiguring, nevertheless, visible changes occur even under mild fluorosis. The affected teeth demonstrate visible changes ranging from the presence of scattered, multiple, small-sized, flat, grey or white spots or flecks on the surface of the enamel in the case of mild fluorosis, through conditions wherein the entire or a major portion of the enamel appears chalky-white, unglazed or dull, and the presence of pitting which may be stained tan, brown or even black in the case of moderate fluorosis. In the case of severe fluorosis, the conditions which are exhibited by the affected teeth appear similar to those described above for moderate fluorosis although the degree of tooth deformity is increased. Disfigurement, in this instance, due to abnormal shape and size of crowns, together with severe pitting and staining, may be pronounced.

Current treatment methods are directed toward resolving the cosmetic effects of fluorosis. These treatments center on either the use of caps which cover the stained and disfigured teeth or the use of bleaching agents for treatment of individual teeth. Each of these techniques has its short comings. In the case of capping, there is the issue of great expense. In the case of bleaching, present procedures call for isolating the tooth to be treated and treating the tooth for up to several weeks. The bleaching technique has limited effectivity and is quite time consuming requiring several applications per affected tooth.

It would, therefore, be highly desirable to have a quick, inexpensive method or removing stains caused by fluorosis.

SUMMARY OF THE INVENTION

This invention comprises a novel method for the reduction or removal of tooth enamel staining due to fluorosis. More specifically, the present invention relates to the use of acid solutions to remove staining. In the practice of the present invention, the affected tooth is isolated and then treated with a swab soaked in an acid solution until the stain is removed.

DESCRIPTION OF THE PREFERRED EMBODIMENTS

The present invention comprises a novel method for the reduction or removal of tooth enamel staining due to fluorosis. The method of the present invention involves isolation of the affected area on a tooth by tooth basis. Each affected tooth may be isolated by means of a conventional rubber dam, although other isolation procedures are possible.

Once isolated, the affected tooth may be treated with a nonabrasive, porous fibrous swab soaked in an acid solution. The nonabrasive, porous, fibrous swab is preferentially a cotton swab, although swabs can be made of other natural or synthetic fibrous material.

The acid solution in which the swab is soaked is preferentially a strong acid, that is to say acids which ionize essentially completely in water thereby producing hydrogen ions and anionic species, although weak acids may be suitable as well. The strong acids which are preferentially used in the practice of the invention are acids which contain a halide atom. Of the halide containing acids, hydrochloric acid is the acid most preferably used.

The acid solution used in the practice of the invention may be a concentrated acid solution or an acid solution diluted in distilled water. As an example, without in any way limiting the scope of the present invention, when the acid is hydrochloric acid, the acid solution used may preferably range from about 6N HCl to about 12N HCl, most preferably about 6N HCl.

The acid soaked swab of the invention may then be held, for example, by means of pressure pincers. The so held swab may then be applied by means of a firm, rotary rubbing motion to the surface of the affected, isolated tooth. The firm, rotary rubbing motion is employed for a period of time sufficient to remove or suitably reduce the stain. When the acid is hydrochloric acid, the period of time ranges from about 2 to about 4 minutes, preferably about 3 minutes in the case of 6N HCl.

Once the stain has been removed or suitably reduced, a neutralizing agent is applied to the affected, isolated tooth. The neutralizing agent used in the practice of present invention is preferably calcium hydroxide, although other neutralizing agents may be employed. When the neutralizing agent is calcium hydroxide, a paste made of calcium hydroxide and water is applied to the treated surface of the affected, isolated tooth for a period of time sufficient to neutralize the acid residue which may be present on the surface of said affected, isolated tooth. The period of time preferentially used in this neutralizing step is approximately 2 minutes when the acid used is hydrochloric acid and the neutralizing agent is calcium hydroxide.

The so treated affected, isolated tooth is then repeatedly rinsed with a neutral aqueous solution, such as, for example, distilled water.

EXAMPLE 1

The tooth to be treated was isolated with a conventional rubber dam. The isolated tooth was then swabbed with an acid solution at a concentration of hydrochloric acid and for the period of time depicted in Table 1. The results were quantified by visual inspection of the tooth prior to and subsequent to treatment, for the reduction of the size of the stain.

TABLE 1

| Concentration of HCl | Time (min) | Results |
| --- | --- | --- |
| 1.5 N | 4 | 10% |
| 3 N | 4 | 30% |
| 4 N | 4 | 50% |
| 5 N | 4 | 80% |
| 6 N | 3 | 100% |
| 7.5 N | 3 | 95% |
| 9 N | 4 | 90% |
| 12 N | 4 | 90% |

The invention treatment for fluorosis-stained teeth does not remove or damage tooth enamel during stain removal. Without being bound by any theory, the inventor speculates that, contrary to prior belief, the observed staining is due to infiltration of staining material into interstices in the tooth enamel. The use of 6N-12N concentrated hydrochloric acid removes the stain-causing material and leaves the tooth enamel stain-free and undamaged.

Additionally, in the invention method, no abrasives are needed to scour or remove tooth enamel. Indeed, non-abrasive applicators are used and the acid itself is non-abrasive. Thus, stain removal is by chemical not mechanical means.

The use of concentrated hydrochloric acid is preferred, and 6N-12N is most preferred. Acid of this concentration need only be applied to the teeth for a short time sufficient to significantly reduce staining, typically 2 to 4 minutes. Further, in most cases only one treatment is needed but in cases of severe staining, up to three treatments may be needed.

From this description of preferred embodiments, those skilled in the art may find many variations and adaptations thereof, and all such variations and adaptations, falling within the scope and spirit of the invention, are intended to be covered by the claims hereafter.

What is claimed is:

1. A method for removing fluorosis stains from teeth of a patient, the method consisting essentially of:
    isolating for treatment a fluorosis-stained tooth;
    treating a surface of the isolated tooth with an abrasive-free solution of hydrochloric acid having a concentration from about 6 to about 12N, for a period of time sufficient to significantly reduce staining thereon without removing enamel from the treated surface; and
    neutralizing any residual acid on the tooth after the treating.

2. The method of claim 1 wherein the treating is continued for from about 3 to about 4 minutes.

3. A method for removing fluorosis stains from teeth of a patient consisting essentially of:
    isolating for treatment a tooth stained with fluorosis;
    treating a surface of the isolated tooth with an abrasive-free solution consisting essentially of from about 6 to about 12N hydrochloric acid for from about 3 to about 4 minutes without removing enamel from the treated surface; and
    neutralizing any residual acid on the treated tooth.

* * * * *